United States Patent
Braun

(10) Patent No.: US 6,881,724 B2
(45) Date of Patent: Apr. 19, 2005

(54) USE OF MAGNESIUM (MG2+) FOR THE PREPARATION OF A THERAPEUTIC COMPOSITION FOR TRANSFECTION OF A POLYNUCLEOTIDE INTO A CELL AND COMPOSITIONS USEFUL IN GENE THERAPY

(75) Inventor: Serge Braun, Dorlisheim (FR)

(73) Assignees: Transgene S.A., Strasbourg (FR); Association Francaise Contre les Myopathies, Paris (FR)

(*) Notice: Subject to any disclaimer, the term of this patent is extended or adjusted under 35 U.S.C. 154(b) by 0 days.

(21) Appl. No.: 10/108,263

(22) Filed: Mar. 28, 2002

(65) Prior Publication Data

US 2002/0156045 A1 Oct. 24, 2002

Related U.S. Application Data

(63) Continuation of application No. 09/408,947, filed on Sep. 30, 1999, now abandoned.

(30) Foreign Application Priority Data

Sep. 30, 1998 (EP) .............................. 98402424

(51) Int. Cl.⁷ .................... A01N 43/04; C07K 17/00
(52) U.S. Cl. ........................ 514/44; 530/350
(58) Field of Search ............... 514/44; 630/350; 530/350

(56) References Cited

U.S. PATENT DOCUMENTS

| | | | | |
|---|---|---|---|---|
| 4,798,789 A | * | 1/1989 | Lee et al. ............... 435/69.52 |
| 5,593,972 A | * | 1/1997 | Weiner ..................... 514/44 |
| 5,693,622 A | | 12/1997 | Wolff et al. |
| 5,703,055 A | | 12/1997 | Felgner et al. |
| 5,831,048 A | * | 11/1998 | Schweighoffer ......... 536/23.1 |
| 5,844,107 A | * | 12/1998 | Hanson ................... 536/23.1 |
| 5,958,684 A | | 9/1999 | Van Leeuwen et al. |
| 5,998,144 A | | 12/1999 | Reff et al. |
| 6,143,518 A | * | 11/2000 | Cameron et al. ......... 435/69.1 |
| 6,258,791 B1 | * | 7/2001 | Braun ..................... 514/44 |
| 6,528,312 B1 | * | 3/2003 | Braun ..................... 435/455 |
| 6,544,523 B1 | * | 4/2003 | Chu ....................... 424/192.1 |

OTHER PUBLICATIONS

Rosenecker (Eur. J. Med. 23(3): 149–156, Mar. 1998.*
Boucher (J. Clin. Invest. 103(4): 441–445 Feb. 1999).*
Davies (Mol. Med Today 4(7): 292–299, Jul. 1998, p. 294, column 2, lines 20–28).*
Alton and Geddes (J. R. Soc. Med 90 Suppl 31: 43–46 1997).*
Boucher (TIG 1.2(3): 81–84, 1996, p. 81, paragraph bridging columns 2 and 3).*
McCluskie et al (Molecular Medicine 5(5): 287–300, 1999).*
Chattergoon et al (FASEB J. 11: 753–763, 1997).*
Karpati et al (Clin. Invest. Med. 17(5): 499–509, 1994).*
Rosenfeld and Collins (Chest 109:241–252, 1996).*
Verma et al (Nature 389: 239–242, 1997).*
Somia and Verma (Nature Reviews Genetics 1: 91–99, 2000).*
Romano et al (Stem Cells 18: 19–39, 2000).*
Anderson (Nature 392:25–30, 1998).*

(Continued)

Primary Examiner—Dave Trong Nguyen
Assistant Examiner—Richard Schnizer
(74) Attorney, Agent, or Firm—Burns, Doane, Swecker & Mathis, L.L.P.

(57) ABSTRACT

Described is the use of magnesium ($Mg^{2+}$) for the preparation of a therapeutic composition for the introduction of a polynucleotide into a cell in vivo.

20 Claims, 3 Drawing Sheets

Figure 1:
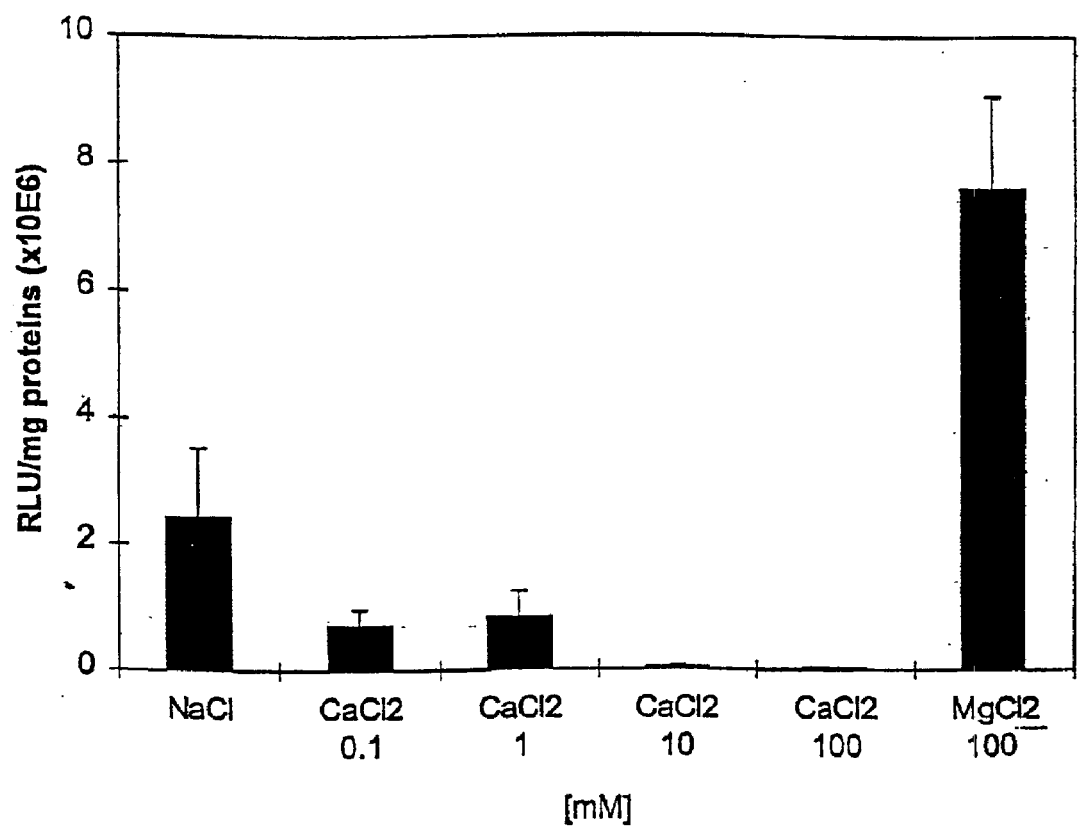

Opposing effects of CaCl2 and MgCl2 on i.m. transfection

OTHER PUBLICATIONS

Derwent Abstract, XP–002099637, "Introducing Gene Cell Virus Serum Serum Free Ingredient Cell Culture Medium Based Aminoacid," Nov. 26, 1996.

Derwent Abstract, XP–002099636, "Cyclic DNA Transductor Acetic Acid Bacteria Solution Contain One More Magnesium Calcium Strontium Barium Manganese," Sep. 25, 1985.

Wells et al., "Evaluation of Plasmid DNA for in Vivo Gene Therapy: Factors Affecting the Number of Transfected Fibers," *Journal of Pharmaceutical Sciences*, 1998, pp. 763–768, vol. 87, No. 6, John Wiley & Sons, New York, New York.

Garcia et al., "Early Stages in *Bacillus subtilis* Transformation: Association Between Homologous DNA and Surface Structures," *Journal of Bacteriology*, 1978, pp. 731–740, vol. 135, No. 3, American Society for Microbiology, Washington, D.C.

Verma et al., "Gene therapy—promises, problems and prospects," *Nature*, 1997, pp. 239–242, vol. 389, Nature Publishing Group, England.

Ledley, "Nonviral Gene Therapy: The Promise of Genes as Pharmaceutical Products," *Human Gene Therapy*, 1995, pp. 1129–1144, vol.6, Mary Ann Liebert, Inc., Larchmont, New York.

Svinarchuk et al., "A New approach to overcome potassium–mediated inhibition of triplex formation," *Nucleic Acids Research*, 1996, pp. 3858–3865, vol. 24, No. 19, Oxford University Press, Oxford, UK.

\* cited by examiner

USE OF MAGNESIUM (MG2+) FOR THE PREPARATION OF A THERAPEUTIC COMPOSITION FOR TRANSFECTION OF A POLYNUCLEOTIDE INTO A CELL AND COMPOSITIONS USEFUL IN GENE THERAPY

This application is a continuation of application Ser. No. 09/408,947, filed on Sep. 30, 1999, now abandoned.

The present invention relates to the use of magnesium ($Mg^{2+}$) for the preparation of a therapeutic composition for improving transfection of a polynucleotide into a cell. Such a composition is useful in gene therapy, vaccination, and any therapeutic or prophylactic situation in which a gene-based product is administered to cells in vivo.

Gene therapy has generally been conceived as principally applicable to heritable deficiency diseases (cystic fibrosis, dystrophies, haemophilias, etc.) where permanent cure may be effected by introducing a functional gene. However, a much larger group of diseases, notably acquired diseases (cancer, AIDS, multiple sclerosis, etc.) might be treatable by transiently engineering host cells to produce beneficial proteins.

Applications are, for example, the treatment of muscular dystrophies or of cystic fibrosis. The genes of Duchenne/Becker muscular dystrophy and cystic fibrosis have been identified and encode polypeptides termed dystrophin and cystic fibrosis transmembrane conductance regulator (CFTR), respectively. Direct expression of these genes within, respectively, the muscle or lung cells of patients should contribute to a significant amelioration of the symptoms by expression of the functional polypeptide in targeted tissues. Moreover, in cystic fibrosis studies have suggested that one would need to achieve expression of the CFTR gene product in only about 5% of lung epithelial cells in order to significantly improve the pulmonary symptoms.

Another application of gene therapy is vaccination. In this regard, the immunogenic product encoded by the polynucleotide introduced in cells of a vertebrate may be expressed and secreted or be presented by said cells in the context of the major histocompatibility antigens, thereby eliciting an immune response against the expressed immunogen. Functional polynucleotides can be introduced into cells by a variety of techniques resulting in either transient expression of the gene of interest, referred to as transient transfection, or permanent transformation of the host cells resulting from incorporation of the polynucleotide into the host genome. Successful gene therapy depends on the efficient delivery to and expression of genetic information within the cells of a living organism. Most delivery mechanisms used to date involve viral vectors, especially adeno- and retroviral vectors. Viruses have developed diverse and highly sophisticated mechanisms to achieve this goal including crossing of the cellular membrane, escape from lysosomal degradation, delivery of their genome to the nucleus and, consequently, have been used in many gene delivery applications in vaccination or gene therapy applied to humans. The use of viruses suffers from a number of disadvantages: retroviral vectors cannot accommodate large-sized DNA (for example, the dystrophin gene which is around 13 Kb), the retroviral genome is integrated into host cell DNA and may thus cause genetic changes in the recipient cell and infectious viral particles could disseminate in the organism or in the environment and adenoviral vectors can induce a strong immune response in treated patients (Mc Coy et al., Human Gene Therapy 6 (1995), 1553–1560; Yang et al., Immunity 1 (1996), 433–442). Nevertheless, despite these drawbacks, viral vectors are currently the most useful delivery systems because of their efficiency.

Non-viral delivery systems have been developed which are based on receptor-mediated mechanisms (Perales et al., Eur. J. Biochem. 226 (1994), 255–266; Wagner et al., Advanced Drug Delivery Reviews 14 (1994), 113–135), on polymer-mediated transfection such as polyamidoamine (Haensler and Szoka, Bioconjugate Chem. 4 (1993), 372–379), dendritic polymer (WO 95/24221), polyethylene imine or polypropylene imine (WO 96/02655), polylysine (U.S. Pat. No. 5,595,897 or FR 2 719 316) or on lipid-mediated transfection (Felgner et al., Nature 337 (1989), 387–388) such as DOTMA (Felgner et al., Proc. Natl. Acad. Sci. USA 84 (1987), 7413–7417), DOGS or Transfectam™ (Behr et al., Proc. Natl. Acad. Sci. USA 86 (1989), 6982–6986), DMRIE or DORIE (Felgner et al., Methods 5 (1993), 67–75), DC-CHOL (Gao and Huang, BBRC 179 (1991), 280–285), DOTAP™ (McLachlan et al., Gene Therapy 2 (1995), 674–622) or Lipofectamine™. These systems present potential advantages with respect to large-scale production, safety, targeting of transfectable cells, low immunogenicity and the capacity to deliver large fragments of DNA. Nevertheless their efficiency in vivo is still limited.

Finally, in 1990, Wolff et al. (Science 247 (1990), 1465–1468) have shown that injection of naked RNA or DNA, without a special delivery system, directly into mouse skeletal muscle results in expression of reporter genes within the muscle cells. This technique for transfecting cells offers the advantage of simplicity and experiments have been conducted that support the usefulness of this system for the delivery to the lung (Tsan et al., Am. J. Physiol. 268 (1995), L1052–L1056; Meyer et al., Gene Therapy 2 (1995), 450–460), brain (Schwartz et al., Gene Therapy 3 (1996), 405–411), joints (Evans and Roddins, Gene therapy for arthritis; In Wolff (ed) Gene therapeutics: Methods and Applications of direct Gene Transfer. Birkhaiser. Boston (1990), 320–343), thyroid (Sikes et al., Human Gen. Ther. 5 (1994), 837–844), skin (Raz et al., Proc. Natl. Acad. Sci. USA 91 (1994), 9519–9523) and liver (Hickman et al., Hum. Gene Ther. 5 (1994), 1477–1483).

Nevertheless, Davis et al. (Human Gene Therapy 4 (1993), 151–159 and Human Mol. Genet. 4 (1993), 733–740) observed a large variability of expression of naked DNA injected into skeletal muscle in vivo which would be insufficient for the treatment of primary myopathies, for example. The authors propose solutions in order to obtain an improvement of the efficiency of gene transfer by preinjecting muscles with a relatively large volume of hypertonic sucrose or with toxins, for example cardiotoxin isolated from snake, in order to stimulate regeneration of muscles. Nevertheless, these methods, although promising, would not be applicable for human treatment.

Thus, the available delivery methods are not satisfactory in terms of safety or efficiency for their implementation in in vivo gene therapy.

Therefore, the technical problem underlying the present invention is the provision of improved methods and means for the delivery of nucleic acid molecules in gene therapy.

This technical problem is solved by the provision of the embodiments as defined in the claims.

Thus, the present invention relates to the use of magnesium ($Mg^{2+}$) for the preparation of a therapeutic composition for transfecting a polynucleotide into a cell in vivo. It was surprisingly found that the specific addition of magnesium when transfecting a polynucleotide into vertebrate tissue leads to a dramatic improvement of the transfection efficiency. Thus, the present invention preferably relates to the use of magnesium ($Mg^{2+}$) for the preparation of a pharmaceutical composition for an improved transfection of a polynucleotide into a cell. The term "improved transfection" in the scope of the present invention means, in this regard, a more efficient uptake of a polynucleotide by cells when magnesium ($Mg^{2+}$) is present compared to an introduction performed without magnesium. This can be determined by comparing the amount of the polynucleotide taken up without the use of magnesium and comparing this amount with the amount taken up by the cells when using magnesium under the same experimental conditions. Preferably, the improved transfection can be determined by a higher amount of expression of the polynucleotide transferred into the cells when using magnesium ($Mg^{2+}$) in comparison to a situation where no magnesium ($Mg^{2+}$) is used.

The therapeutic compositions prepared according to the use of the present invention are particularly useful for the delivery of polynucleotides to cells or tissues of a subject in the scope of a gene therapeutic method but are not limited to such use. The term "gene therapy method" is preferably understood as a method for the transfection of a polynucleotide into cells in vivo. "Gene therapy" in particular concerns the case where the gene product is expressed in a target tissue as well as the case where the gene product is excreted, especially into the blood stream.

In the scope of the present invention the term "transfection" means the transfer of the polynucleotide into a cell wherein the polynucleotide is not associated with viral particles. Thus, transfection is to be distinguished from infection which relates to polynucleotides associated with viral particles.

Magnesium ($Mg^{2+}$) has been shown to:
- reduce the interaction of virus with water leading to a decline in the extent of water penetration into the viral capside (Chen et al., Arch. Biochem. Biophys. 342 (1997), 108–116);
- bind to nucleic acids (Rowatt et Williams, J. Inorg. Biochem. 46 (1992), 87–97);
- influence DNase I inactivation by heat treatment (Bickler et al., Biotechniques 13 (1992), 64–6);
- be involved in metabolic functions such as glycolysis, RNA/DNA synthesis or protein synthesis (Günther, Magnesium 5 (1986), 53–9);
- act as a cofactor for the binding of the C protein to its specific site in DNA (De et al., Biochemistry 37 (1998), 3831–8) or of the EcoRV restriction endonuclease (Thielking et al., Biochemistry 31 (1992), 3727–32).

Japanese patent application (JO8308573) abstract discloses an in vitro method of introducing a gene into cells by using a virus as vector, prepared in a virus-infection medium which contains serum-free ingredients or divalent metal ions selected from Mg, Ca and Zn combined with a cell culture medium based on amino acids.

The term "magnesium ($Mg^{2+}$)" as used herein, means the divalent cation of magnesium. Such a product is commercially available associated with one or several biologically acceptable anions, such as, for example, bisulfite, chromate, fluoride, gluconate, acetate, hydroxide, iodide, methoxide, oxide, phosphate, sulfate, chloride, bromide, etc (see Aldrich catalogue, 1994/1995, for example). According to a preferred embodiment, said magnesium ($Mg^{2+}$) is associated with chloride ($MgCl_2$).

In a preferred embodiment the amount of magnesium in the compositions prepared according to the use of the present invention ranges between about 0.1 to about 100 mM, preferably from about 0.1 to about 10 mM of magnesium, and still preferably is 0.5 mM. This concentration may also be adapted by those skilled in the art in particular cases where magnesium concentration can be affected. For example, when the therapeutic composition further comprises chelating agent, such as EDTA, it would be preferable to improve the magnesium concentration in order to compensate for magnesium depletion due to chelation. This can occur when the polynucleotide has been previously prepared in a buffer such as TE (Tris-EDTA).

In a preferred embodiment the therapeutic composition prepared according to the use of the present invention is in a form for administration into a vertebrate tissue. These tissues include those of muscle, skin, brain, lung, liver, spleen, bone marrow, thymus, heart, lymph, bone, cartilage, pancreas, kidney, gall bladder, stomach, intestine, testis, ovary, uterus, rectum, nervous system, eye, gland, connective tissue, blood, tumor etc. Cells where the improved transfection of a foreign polynucleotide would be obtained are those found in each of the listed target tissues (muscular cells, airway cells, hematopoïetic cells, etc.). The administration may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Transdermal administration is also contemplated, as are inhalation or aerosol administration.

In a preferred embodiment, the therapeutic composition prepared according to the use is for the introduction into muscle tissue, more preferably, by intramuscular injection routes.

In another preferred embodiment, the invention provides the use of magnesium for the preparation of a therapeutic composition for improving transfection of a polynucleotide into a cell wherein said therapeutic composition is administered independently from a second administration consisting in administration of a composition containing at least one polynucleotide. According to the present invention, the first administration can be done prior to, concurrently with or subsequent to the second administration, and vice-versa. The therapeutic composition administration and second administration can be performed by different or identical delivery routes (systemic delivery and targeted delivery, or targeted deliveries for example). In a preferred embodiment, each should be done into the same target tissue and most preferably by injection.

In a further preferred embodiment of the use according to the present invention, the therapeutic composition further comprises at least one polynucleotide. In a particularly preferred embodiment, the polynucleotide which is contained in the composition, contains and is capable of functionally expressing a gene in said cell. The polynucleotide may be a DNA or RNA, single or double stranded, linear or circular, natural or synthetic, modified or not (see U.S. Pat. No. 5,525,711, U.S. Pat. No. 4,711,955 or EP-A 302 175 for modification examples). It may be, inter alia, a genomic DNA, a cDNA, an mRNA, an antisense RNA, a ribosomal RNA, a ribozyme, a transfer RNA or DNA encoding such RNAs. "Polynucleotides" and "nucleic acids" are synonyms with regard to the present invention. The polynucleotide may also be in the form of a plasmid or linear polynucleotide which contains at least one expressible sequence of nucleic acid that can generate a polypeptide, a ribozyme, an antisense RNA or another molecule of interest upon delivery to a cell. The polynucleotide can also be an oligonucleotide which is to be delivered to the cell, e.g., for antisense or ribozyme functions.

In a particularly preferred embodiment of the invention the polynucleotide is a naked polynucleotide (Wolff et al., Science 247 (1990), 1465–1468) or is a polynucleotide associated or complexed with a polypeptide, with the proviso that when said polypeptide is a viral polypeptide, then said polynucleotide combined with the viral polypeptide does not form infectious viral particles, or with a cationic compound or with any component which can participate in the protection and uptake of the polynucleotide into the cells (see Ledley, Human Gene Therapy 6 (1995), 1129–1144 for a review). Cationic compounds to which the polynucleotide is complexed are preferably cationic lipids, especially those disclosed in WO 98/34910. Both DNA or RNA can be delivered to cells to form therein a polypeptide of interest. Preferably, the polynucleotide present in the therapeutic composition is in the form of plasmid DNA. If the polynucleotide contains the proper genetic information, it will direct the synthesis of relatively large amounts of the encoded polypeptide. When the polynucleotide delivered to the cells encodes an immunizing polypeptide, the use according to the invention can be applied to achieve improved and effective immunity against infectious agents, including intracellular viruses, and also against tumor cells. The genetic informations necessary for expression by a target cell comprise all the elements required for transcription of said DNA into mRNA and for translation of mRNA into polypeptide. Transcriptional promoters suitable for use in various vertebrate systems are well known. For example, suitable promoters include viral promoters like RSV, MPSV, SV40, CMV or 7.5 k, vaccinia promoter, inducible promoters, etc. The polynucleotide can also include intron sequences, targeting sequences, transport sequences, sequences involved in replication or integration. Said sequences have been reported in the literature and can be readily obtained by those skilled in the art. The polynucleotide can also be modified in order to be stabilized with specific components as spermine.

In general, the concentration of the polynucleotide in the composition is from about 0.1 $\mu$g/ml to about 20 mg/ml. According to the invention, the polynucleotide can be homologous or heterologous to the target cells into which it is introduced. Advantageously said polynucleotide encodes all or part of a polypeptide, especially a therapeutic or prophylactic polypeptide. A polypeptide is understood to be any translational product of a polynucleotide regardless of size, and whether glycosylated or not, and includes peptides and proteins. Therapeutic polypeptides include as a primary example those polypeptides that can compensate for defective or deficient proteins in an animal or human organism, or those that act through toxic effects to limit or remove harmful cells from the body. They can also be immunity conferring polypeptides which act as endogenous immunogens to provoke a humoral or cellular response, or both. Examples of polypeptides encoded by the polynucleotide are enzymes, hormones, cytokines, membrane receptors, structural polypeptides, transport polypeptides, adhesines, ligands, transcription factors, traduction factors; replication factors, stabilization factors, antibodies, more especially CFTR, dystrophin, factors VIII or IX, E6 or E7 from HPV, MUC1, BRCA1, interferons, interleukin (IL-2, IL-4, IL-6, IL-7, IL-12, GM-CSF (Granulocyte Macrophage Colony Stimulating Factor), the tk gene from Herpes Simplex type 1 virus (HSV-1), p53 or VEGF. The polynucleotide can also code for an antibody. In this regard, antibody encompasses whole immunoglobulins of any class, chimeric antibodies and hybrid antibodies with dual or multiple antigen or epitope specificities, and fragments, such as F(ab)$_2$, Fab', Fab including hybrid fragments and anti-idiotypes (U.S. Pat. No. 4,699,880).

In a further preferred embodiment the composition further comprises at least one component selected from the group consisting of chloroquine, protic compounds such as propylene glycol, polyethylene glycol, glycerol, ethanol, 1-methyl L-2-pyrrolidone or derivatives thereof, aprotic compounds such as dimethylsulfoxide (DMSO), diethylsulfoxide, di-n-propylsulfoxide, dimethylsulfone, sulfolane, dimethyl-formamide, dimethylacetamide, tetramethylurea, acetonitrile or derivatives. Said composition can also comprises at least one component selected from the group consisting of cytokines, especially interleukin-10 (IL-10), and nuclease inhibitors such as, for example, actin G.

In another preferred embodiment the composition prepared according to the use of the invention can be used in a method for the therapeutic treatment of humans or animals. In this particular case, the composition may also comprise a pharmaceutically acceptable injectable carrier (for examples, see Remington's Pharmaceutical Sciences, 16$^{th}$ ed. 1980, Mack Publishing Co). The carrier is preferably isotonic, hypotonic or weakly hypertonic and has a relatively low ionic strength, such as provided by a sucrose solution. Furthermore, it may contain any relevant solvents, aqueous or partly aqueous liquid carriers comprising sterile, pyrogen-free water, dispersion media, coatings, and equivalents, or diluents (e.g;, Tris-HCl, acetate, phosphate), emulsifiers, solubilizers or adjuvants. The pH of the pharmaceutical preparation is suitably adjusted and buffered in order to be useful in in vivo applications.

In another aspect the present invention also relates to a process for transfecting a polynucleotide into cells wherein said process comprises contacting said cells with a composition prepared according to the use of the invention before, simultaneously or after contacting them with the polynucleotide. This process may be applied by direct administration of said composition to cells of the animal in vivo. According to the practice of the invention, targeted "cells" and "in vivo administration route" are defined as above described.

Preferably, muscle is used as a site for the delivery and expression of a polynucleotide in a number of therapeutic applications because animals have a proportionately large muscle mass which is conveniently accessed by direct injection through the skin. Accordingly, in a preferred case, the invention concerns a process for introducing a polynucleotide, preferably in naked form, into muscle cells in vivo, comprising the steps of administering in vivo at least a polynucleotide and magnesium, preferably intramuscularly, whereby the polynucleotide is introduced into muscle cells of the tissue. The polynucleotide may encode a therapeutic polypeptide that is expressed by the muscle cells and eventually secreted into the blood stream after the contacting step to provide therapy to the vertebrate. Similarly, it may encode an immunogenic polypeptide that is expressed by the muscle cells after the contacting step and which generates an immune response, thereby immunizing the vertebrate. One important aspect of the invention is a process for the treatment of muscular dystrophy wherein said polynucleotide operatively codes for dystrophin. Preferably, the composition is introduced into the muscle tissue.

Finally, the present invention relates to the use of Magnesium ($Mg^{2+}$) for improving transfection of a polynucleotide into a cell.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the claims, the invention may be practiced otherwise than as specifically described.

FIG. 1: shows the opposing effects of $CaCl_2$ and $MgCl_2$ on intramuscular transfection of pTG11033. Luciferase activity of mouse right and left tibialis anterior muscles measured 7 days after injection with 25 μg plasmid added with NaCl 0.9% buffer (Control, NaCl) or with either 0.1 to 100 mM of $CaCl_2$ or 100 mM $MgCl_2$. Bars are means of RLU (Relative Light Unit) per minute per mg protein+/–s.e.m. of 6 determinations.

Figure 2:
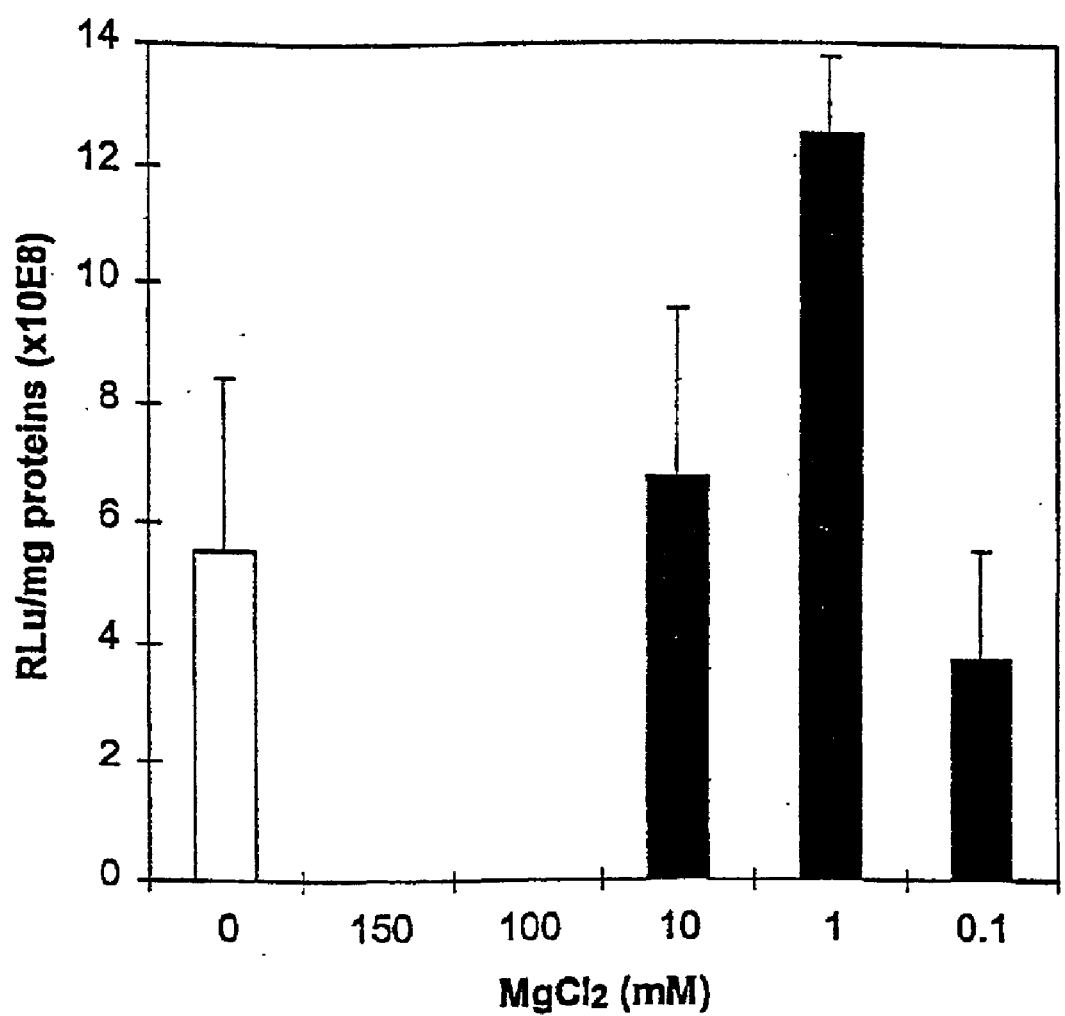
Figure 3:
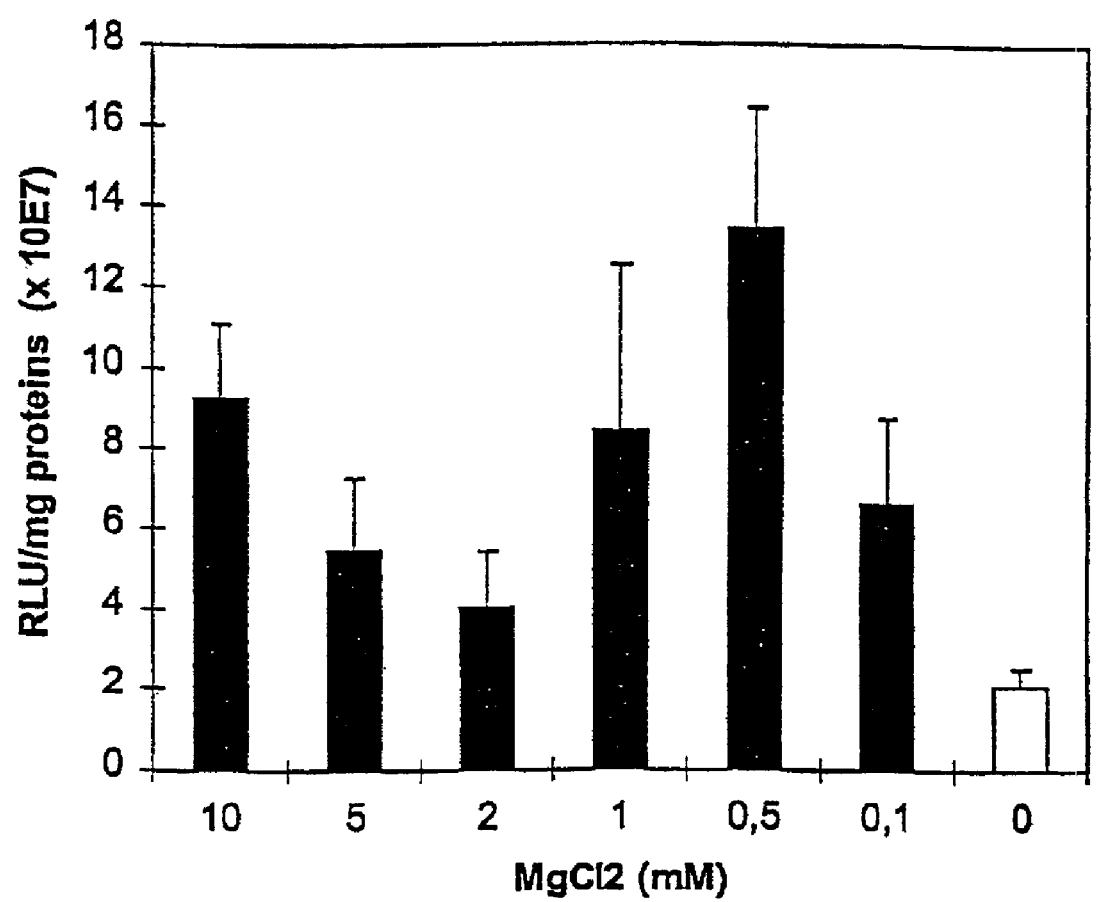

FIGS. 2 and 3: show the $MgCl_2$ dose-effect on intramuscular transfer of the luciferase-plasmid (pTG11033). Bars are means of RLU per minute per mg protein+/–s.e.m of 6 determinations. Luciferase activity was measured 7 days after injection of 25 μg plasmid into C57BL/10 mice (4 mice per group) added with either NaCl 0.9% (empty bars) or different concentrations of $MgCl_2$ (black bars).

The following examples illustrate the invention.

Material and Methods

The following materials and methods are used in the examples.

1. Intramuscular Administration of Plasmid/Divalent Ion Composition

Plasmid DNA (pTG11033: CMV promoter, β-globin intron, luciferase cassette—WO 98/34910) was prepared according to Bischoff et al., Analytical Biochemistry 254 (1997), 69–81. Prior to intramuscular injection the tested molecules were mixed with the plasmid DNA preparation. 25 μg of plasmid DNA were injected per muscle into 5 to 10 week-old C57BL/10 mice. The 2 tibialis anterior (right and left) muscles were injected (each muscle was considered as a sample). Furthermore, for each condition, both the lowest and highest luciferase acitvity values were omitted, which means number of sample per condition=(2×number of mice per condition)−2.

2. Muscle Biopsies and Luciferase Measurement

One week after injection of the composition, the mice were killed and the tibialis anterior muscles were retrieved and frozen.

Luciferase activity was quantified on whole muscle extracts using a conventional measurement kit (Luciferase Assay System, Promega). Briefly, muscles were ground separately and diluted in 200 μl of reporter lysis buffer (Promega). 10 μl-samples were placed in 96 well-plates and mixed with 100 μl of substrate. Luciferase activity was expressed as number of RLU emitted per minute, per mg of protein.

3. Protein Determination

Protein was measured on 10 μl samples using a VCA Protein Assay kit (Pierce).

EXAMPLE 1

In Contrast to Calcium ($Ca^{2+}$) Magnesium ($Mg^{2+}$) Increases Gene Transfer of a Plasmid Comprising the Luciferase Gene In this example, the stock solution of plasmid pTG11033 was prepared in TE buffer (Tris 10 mM-EDTA 1 mM) at a nucleic acid concentration of 1 μg/μl.

Stock solutions of $CaCl_2$ and $MgCl_2$ were prepared in water at a concentration of 1M.

Four C57Bl/10 mice were injected per condition into the right and left tibialis anterior muscle with different compositions comprising pTG11033 (25 μg/muscle) and various concentrations of calcium chloride ($CaCl_2$; 100, 10, 1, 0.1 mM) or magnesium chloride ($MgCl_2$; 100 mM). The control experiment is performed according to the same condition except that no divalent ion is added and that 5 μl of NaCl 0.9% is added. The injected volume was 30 μl.

The results are presented in FIG. 1. They show that addition of $CaCl_2$ leads to a dramatic inhibition of luciferase activity of the injected muscles (from 3 to 100 fold drop depending on the final concentration of $CaCl_2$) even at the lowest concentration tested (0.1 mM). Conversely, $MgCl_2$ allowed an increased luciferase activity in the injected muscles (around 3 times in the present example).

EXAMPLE 2

Serial Dilution of $MgCl_2$

In this example, the plasmid pTG11033 was prepared in NaCl 0.9% and stocked at 1 μg/μl. Serial dilution of $MgCl_2$ solution were prepared in NaCl 0.9% and added to the stock pTG11033 in a final volume of 30 μl. The control contained the same quantity of the plasmid added with 5 μl of NaCl 0.9%. Ionic strength of $MgCl_2$ solutions was balanced with appropriate volumes of water according to methods well known to the person skilled in the art.

As previously described, four mice were injected per condition.

The results are presented in FIG. 2. They show that $MgCl_2$ has an influence on luciferase activity of the injected muscles. The lowest dose (0.1 mM) of $MgCl_2$ had no effect on the injected muscle luciferase activity, wherease luciferase activity was higher in muscles injected in the presence of 1 mM $MgCl_2$, similar to the control when 10 mM $MgCl_2$ was used, and strongly inhibited at higher concentrations.

A more precise range of concentrations of $MgCl_2$ (0.1, 0.5, 1, 2, 5, 10 mM) was evaluated using the same conditions as described for Example 2. It was found that the optimal concentration was 0.5 mM when a preparation of plasmid pTG11033 in 0.9% NaCl was used.

What is claimed is:

1. A method for transfer of a naked polynucleotide into cells of a subject in vivo comprising:

preparing a composition comprising at least one naked polynucleotide and about 0.5 mM to about 5 mM magnesium ($Mg^{2+}$); and, administering said composition into said subject, resulting in transfer of said naked polynucleotide into said cells.

2. The method of claim 1, wherein said magnesium is provided as magnesium chloride ($MgCl_2$).

3. The method of claim 1, wherein said administration is made by intradermal, subdermal, intravenous, intramuscular, intranasal, intracerebral, intratracheal, intraarterial, intraperitoneal, intravesical, intrapleural, intracoronary or intratumoral injection.

4. The method of claim 1, wherein said administration is made into a lung by inhalation or aerosol administration.

5. The method of claim 1, wherein said administration is made into a muscle.

6. The method of claim 1, wherein said polynucleotide contains a gene of interest.

7. The method of claim 1, wherein said polynucleotide is present in a concentration ranging from about 0.1 μg/ml to about 20 mg/ml.

8. The method of claim 6, wherein said gene encodes all or part of dystrophin.

9. The method of claim 1, wherein said composition further comprises at least one component selected from the group consisting of chloroquine, protic compounds, and aprotic compounds.

10. The method of claim 1, wherein said composition further comprises at least one component selected from the group consisting of cytokines and actin-G.

11. The method of claim 1, wherein the composition further comprises a pharmaceutically acceptable injectable carrier.

12. A method for the transfer of a polynucleotide into cells of a subject in vivo comprising:

administering at least one naked polynucleotide into a target tissue of said subject; and administering a composition comprising about 0.5 mM to about 5 mM magnesium ($Mg^{2+}$) into said target tissue, resulting in transfection of said polynucleotide into said cells;

wherein said administration of the composition comprising magnesium ($Mg^{2+}$) is done prior to, simultaneous to, or subsequent to said administration of at least one polynucleotide.

13. The method of claim 1, wherein said composition contains from about 0.5 mM to about 1 mM of magnesium ($Mg^{2+}$).

14. A method for the transfer of a polynucleotide into cells of a subject in vivo comprising:

administering a composition comprising about 0.5 mM to about 5 mM magnesium ($Mg^{2+}$) into a target tissue of said subject; and, in a separate second administration step, administering a composition containing at least one naked polynucleotide into the same target tissue of said subject, resulting in transfection of said polynucleotide into said cells.

15. The method of claim 14, wherein the administration of magnesium ($Mg^{2+}$) is performed prior to said second administration.

16. In a method for the transfer of a polynucleotide into cells of a subject in vivo comprising preparing a composition comprising at least one naked polynucleotide and administering said composition to said subject, the improvement comprising:

including about 0.5 mM to about 5 mM magnesium ($Mg^{2+}$) in said composition.

17. The method of claim 16, wherein said magnesium is provided as magnesium chloride ($MgCl_2$).

18. In a method for the transfer of a polynucleotide into cells of a subject in vivo comprising preparing a composition comprising at least one naked polynucleotide and administering said composition into a target tissue of said subject, the improvement comprising:

administering a composition comprising about 0.5 mM to about 5 mM magnesium ($Mg^{2+}$) into said target tissue of said subject;

wherein said administration of the composition comprising magnesium ($Mg^{2+}$) is done prior to, simultaneous to, or subsequent to said administration of at least one polynucleotide.

19. In a method for the transfer of a polynucleotide into cells of a subject in vivo comprising administering a composition comprising at least one naked polynucleotide into a target tissue of said subject, the improvement comprising:

administering about 0.5 mM to about 5 mM magnesium ($Mg^{2+}$) into said target tissue of said subject.

20. The method of claim 19, wherein the administration of magnesium ($Mg^{2+}$) is performed prior to the administration of the composition comprising at least one polynucleotide.

* * * * *